United States Patent
O'Neal et al.

(10) Patent No.: US 11,692,165 B2
(45) Date of Patent: Jul. 4, 2023

(54) PIVOT ARM SYSTEMS FOR MIXING IN BIOREACTORS

(71) Applicant: ExxonMobil Technology and Engineering Company, Annandale, NJ (US)

(72) Inventors: Everett J. O'Neal, Asbury, NJ (US); Louis R. Brown, La Jolla, CA (US); Patrick L. Hanks, Bridgewater, NJ (US); Mark A. Deimund, Jersey City, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 297 days.

(21) Appl. No.: 16/891,114

(22) Filed: Jun. 3, 2020

(65) Prior Publication Data
US 2021/0047608 A1  Feb. 18, 2021

Related U.S. Application Data

(60) Provisional application No. 62/886,230, filed on Aug. 13, 2019.

(51) Int. Cl.
| | | |
|---|---|---|
| *C12N 1/00* | (2006.01) | |
| *C12N 1/12* | (2006.01) | |
| *C12M 1/00* | (2006.01) | |
| *B01F 27/83* | (2022.01) | |
| *B01F 27/85* | (2022.01) | |
| *B01F 27/191* | (2022.01) | |
| *B01F 101/48* | (2022.01) | |

(52) U.S. Cl.
CPC .............. *C12N 1/12* (2013.01); *B01F 27/191* (2022.01); *B01F 27/83* (2022.01); *B01F 27/85* (2022.01); *C12M 23/18* (2013.01); *B01F 2101/48* (2022.01)

(58) Field of Classification Search
CPC ...... C12M 23/18; C12N 1/12; B01F 2101/48; B01F 27/83; B01F 27/191; B01F 27/85
See application file for complete search history.

(56) References Cited

U.S. PATENT DOCUMENTS

| | | |
|---|---|---|
| 3,855,370 A | 12/1974 | Dodd |
| 2009/0071064 A1 | 3/2009 | Machacek et al. |
| 2010/0325948 A1* | 12/2010 | Parsheh ................. A01G 33/00 47/1.4 |
| 2017/0158995 A1* | 6/2017 | Garvik ................... C12M 27/06 |

\* cited by examiner

*Primary Examiner* — Anshu Bhatia
(74) *Attorney, Agent, or Firm* — Shook, Hardy & Bacon, LLP

(57) ABSTRACT

A system for growing algae includes a pivot arm pivotally coupled to a pivot connection positioned in a pond containing water and algae, and a mixing device coupled to the pivot arm and extending into the pond to mix the water and the algae as the pivot arm rotates.

20 Claims, 4 Drawing Sheets

PIVOT ARM SYSTEMS FOR MIXING IN BIOREACTORS

CROSS-REFERENCE TO RELATED APPLICATIONS

This application claims priority to U.S. Provisional Application No. 62/886,230 filed Aug. 23, 2019, which is herein incorporated by reference in its entirety.

BACKGROUND OF THE INVENTION

Concerns about climate change, carbon dioxide ($CO_2$) emissions, and depletion of subterranean oil and gas resources have led to widespread interest in the production of biofuels from algae and microalgae. As used herein, the term "biofuel" refers to any type of fuel produced from algae, and the term "algae" will include microalgae, unless explicitly distinguished.

As compared to other plant-based feedstocks, algae have higher $CO_2$ fixation efficiencies and growth rates, and growing algae can efficiently utilize wastewater and industrial gases as nutrient sources. The biomass of algae stores increasing quantities of lipids as it grows. Methods for harvesting and utilizing algae involve extracting and converting their stored lipids and carbohydrates into renewable biofuels, such as diesel and jet fuel, or into other hydrocarbons, as examples.

Algae biomass is generally grown in a water slurry contained in a light-driven bioreactor or "photobioreactor" (PBR) using photosynthetic algae strains. Types of photobioreactors include open and closed ponds and closed or open reactor vessels, as examples. Various strains of algae are classified as photoautotrophic organisms, or organisms that can survive, grow and reproduce with energy derived entirely from the sun through the process of photosynthesis. Photosynthesis, aided by other cellular biochemical processes, is essentially a carbon recycling process through which inorganic $CO_2$ is absorbed and combined with solar energy, nutrients, and water to synthesize carbohydrates, lipids, and other compounds necessary to algae life. In addition to production of lipids and carbohydrates for biofuel production, the benefits of growing and harvesting algae includes utilization of carbon dioxide and production of oxygen.

Effective PBR designs are capable of sustaining high-density cultures while enabling efficient light delivery and gas exchange. PBRs may be open or closed to the atmosphere. A common type of open PBR used for commercial-scale algal cultivation is the open raceway pond. In a conventional open raceway pond, paddle wheels held at fixed locations are used to move the bulk water slurry in the pond, causing essentially all the slurry to circulate around the raceway. While the raceway pond design has advantages, it includes fundamental limitations in delivery of sufficient light to maintain high photosynthetic rates. Uneven light distribution causes the algae to be overexposed at the surface and underexposed below the light penetration depth.

In addition, conventional raceway ponds have limited capability for improving mass transfer rates between the pond water and the algae, and thus are subject to limits of scale, referring to a practical size limit for equipment. Mass transfer rates refer to the delivery of carbon dioxide and nutrients to the growing algae and to the removal of byproducts, such as oxygen, from the algae. Mass transfer rates may be increased by circulating the bulk fluid in the pond and by increasing the velocity of the circulating fluid to achieve greater mixing of fluid. Moving the bulk fluid to improve light distribution or mass transfer rate, as is done in raceway ponds, is energy intensive due to the quantities of water than must be moved or the velocities that must be achieved. As examples, the water flow may be millions of barrels per day through a conventional 10 kbd (thousand barrels per day) oil production facility, and the power required for fluid circulation may increase exponentially or by a power function with respect to velocity, substantially influencing the operational cost. Furthermore, high-productivity strains of algae (e.g. strains that produce >20 grams-biomass/$m^3$-of-pond/day) may require much higher mass transfer rates than is acknowledged in the literature.

Conventional raceway ponds cannot easily ramp their mass transfer rates due to the inertia of large machinery (e.g., paddlewheels or pumps) and the large water volumes that must be circulated. For some systems, the physical size of a paddle wheel or pump may be increased to improve fluid velocity or volumetric flow rate and to improve the resulting mass transfer rate, but size is limited by constraints. Some conventional systems may be built with additional paddle wheels or pumps operating in series in a shared raceway or with additional parallel raceways to achieve a higher mass transfer rate, but ultimately a system will reach an economic or design limit, presenting a limitation of scale.

Therefore, algae growth systems that provide greater uniformity of light distribution to greater portions of the algae or that provide increased mass transfer rates more economically are desirable.

SUMMARY OF THE INVENTION

The present disclosure is related to growing algae for biofuel production and, more particularly, to improved designs for photobioreactors and systems used to grow algae.

In some embodiments disclosed herein, a system for growing algae includes a pivot arm pivotally coupled to a pivot connection positioned in a pond containing water and algae, and a mixing device coupled to the pivot arm and extending into the pond to mix the water and the algae as the pivot arm rotates.

In some embodiments disclosed herein, a method for growing algae includes introducing algae and water into a pond having a pivot arm pivotally coupled to a pivot connection positioned in the pond, rotating the pivot arm about a pivot axis extending through the pivot connection, and mixing the water and the algae with a mixing device coupled to the pivot arm as the pivot arm rotates.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

This disclosure presents systems for growing algae in a pond. The systems may be well-suited for large-scale, e.g. commercial-scale, production of algae for biofuel or other hydrocarbons. The disclosed systems include fluid mixing devices that are configured to move through the water slurry of the pond rather remaining stationary relative to the pond. The mixing devices induce localized movement or circulation of the water slurry in the vicinity of the mixing devices. In some embodiments, the mixing devices may also induce bulk movement or circulation of the water slurry in the pond while the mixing devices move through the pond. If bulk fluid movement is induced, the resulting flow rate may be substantially less than the flow rate induced in a conventional pond with paddle wheels or pumps.

The disclosed systems are intended to minimize unnecessary water flow, which is energy intensive and expensive on the scale used for algae-based oil production facilities. The systems disclosed herein may also provide improved light distribution and substantially higher mass transfer rates (e.g., delivery of carbon dioxide and nutrients and removal of byproducts) than can be provided by conventional raceway pond algae growth systems. While the systems disclosed herein are well-suited to various algae strains, they may be particularly suited for high-productivity strains of algae, which require higher mass transfer rates than various other strains of algae. These improvements may be achievable with an algae growing system that includes a mixing device configured to travel through the pond.

Figure 1:
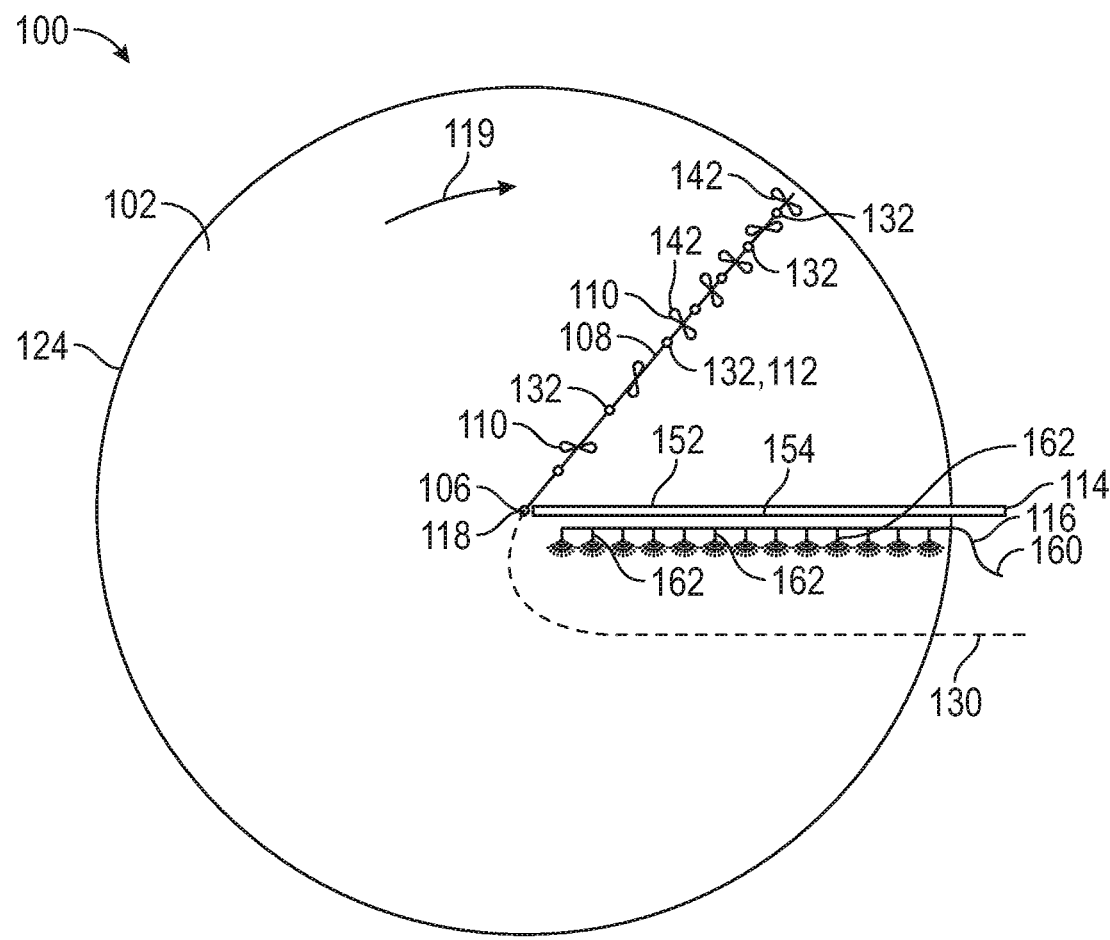
FIG. 1 is a top-view diagram of an example system for growing algae in a pond, according to various embodiments of the present disclosure.
Figure 2:
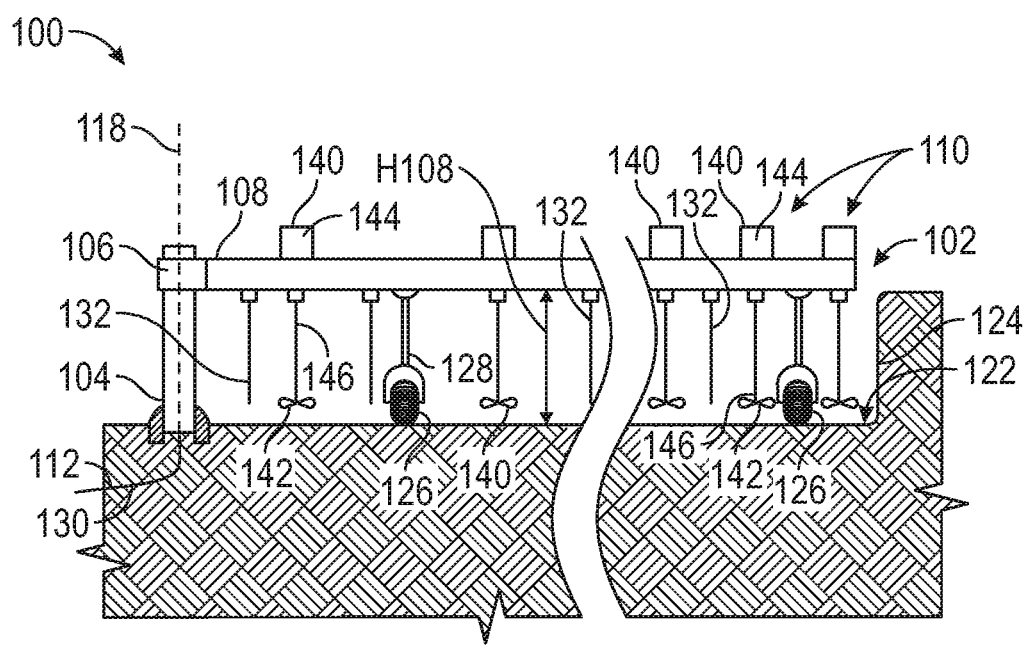
FIG. 2 illustrates a side view of the system of FIG. 1.

FIG. 1 is a schematic top view of an example system 100 for growing algae, according to one or more embodiments, and FIG. 2 illustrates a side view of the system 100. System 100 is shown installed in and incorporated with a lagoon or pond 102. System 100 may be described herein and otherwise characterized as an "open" photobioreactor. System 100, like the other systems disclosed herein, may be configured and fabricated independently of pond 102. Pond 102 is defined by a pond bottom 122 and a pond perimeter 124, which in this example is circular. Pond 102 may contain a mixture or slurry that may include water, algae, dissolved gases, and nutrients. The water slurry of pond 102 includes an upper surface, and in some embodiments, the location of pond perimeter 124 may vary depending on the height of the upper surface of the pond 102.

As illustrated, system 100 includes a pivot arm 108 coupled to a pivot connection 106 mounted at a stationary base, which in this example includes a pivot post 104 disposed in the center of the pond 102. Pivot arm 108 extends generally horizontal and radially outward from pivot post 104. System 100 further includes a mixing device 110 coupled to pivot arm 108, a sparging device 112 coupled to pivot arm 108, a skimming trough 114 extending across a portion of pond 102, and a water supply device 116.

Pivot post 104 and pivot connection 106 define a vertical pivot axis 118 that is the center of rotation for pivot arm 108. Pivot arm 108 is configured to travel through an arcuate or circular sweeping path about pivot axis 118 to move mixing device 110 through the water in pond 102 to mix the water. In general, mixing or moving the water in pond 102 refers to mixing or moving the water as well as the nutrients, algae, gases, etc. that may be suspended, dissolved, settled, or otherwise physically associated with pond 102.

In some embodiments, pivot arm 108 may travel in a clockwise angular direction 119 (FIG. 1) about axis 118, but could alternatively travel counter-clockwise, without departing from the scope of the disclosure. One or more wheels 126 and corresponding support legs 128 may support pivot arm 108 and facilitate travel along pond bottom 122. In some embodiments, pivot arm 108 may be actuated to move (rotate) from pivot post 104, such as via a central motor that rotates pivot arm 108. In other embodiments, however, one or more of wheels 126 may be driven independently by a motor (e.g., electric, hydraulic, pneumatic, combustion, etc.).

Pivot arm 108 is disposed a height H108 from the pond bottom 122. In some embodiments, height H108 may position the arm 108 above the upper surface of pond 102. In other embodiments, however, pivot arm 108 may be disposed within the depth of pond 102 (e.g., within the water).

Sparging device 112 includes a sparging supply line 130 coupled to a plurality of sparging tubes or sparging nozzles 132 that extend from pivot arm 108 into pond 102. In some embodiments, supply line 130 may extend through pivot post 104, through pivot connection 106, and into pivoting arm 108 to fluidly couple to sparging nozzles 132. Pivot connection 106 includes a rotatable coupling incorporated into supply line 130 to accommodate the rotation of a downstream portion of supply line 130 disposed in/on pivot arm 108 relative to an upstream portion of supply line 130 disposed in post 104, without leaking fluid. Sparging device 112 is configured to provide a supply of one or more gases to be injected into pond 102, such as carbon dioxide, flue gas, air, or another gas containing carbon dioxide. Thus, the carbon dioxide may come from any suitable source, including atmospheric air, an exhaust stream from a combustion process, or a storage location such as a tank or a geological formation. In addition to providing algae with carbon dioxide for growth, the gas(es) discharged from sparging nozzles 132 may cause mixing of the algae slurry, which may improve the absorption of carbon dioxide or may cause algae to circulate towards the surface of pond 102 to receive light more uniformly. Thus, sparging nozzles 132 may also operate as mixing tools. In some embodiments, sparging nozzle 132 is configured as tube that includes multiple holes along a length or around a circumference of the tube.

Mixing device 110 is configured to cause mixing action in pond 102 to increase the uniformity of light distribution to the algae in the pond 102 or to increase the mass transfer rates of gases provided by the sparging device 112 to the algae in the pond 102. Mixing device 110 may include one or more mixers 140 attached to pivot arm 108. In embodiments with two or more mixers 140, mixers 140 may be spaced apart from each other along the pivot arm 108. In some embodiments, the distance between adjacent mixers 140 may decrease in the outward radial direction to provide greater uniformity of mixing within pond 102 as the pivot arm 108 rotates.

Each mixer 140 may include a mixing tool 142 powered by a motor 144 for rotation. In some embodiments, motors 144 may be electric motors mounted to pivot arm 108, and one mixing tool 142 may be coupled to each motor 144 by a downward extending shaft 146 or another connecting device. A mixing tool 142 may be, as an example, a propeller-type blade (as shown), a screw profile (e.g., an auger, an Archimedes screw, etc.), a jet, a nozzle, a wave generator, or another suitable arrangement configured to agitate the fluid and otherwise cause the fluid to circulate between lower and upper depths of the pond 102. In some embodiments, mixing tools 142 closer to perimeter 124 of pond 102 may be operated at an increased intensity in contrast to mixing tools 142 located closer to pivot axis 118. This may prove advantageous in compensating for tangential fluid flow velocities.

In some embodiments, mixing tools 142 may be disposed near pond bottom 122 and may be configured to induce vertical movement of fluid in pond 102. As examples, mixing tools 142 may move water and algae upward or downward, due either to the direct influence of mixing tools 142 or due to fluid circulation induced indirectly elsewhere in the pond 102 by the mixing tools 142. A vertically upward motion generated by mixing device 110 may cause or encourage vertically upward motion of the algae growing in pond 102, making the algae or a ripe portion of the algae available at the surface of pond 102 to be harvested. Moreover, the fluid motion in pond 102 caused by mixing device 110 may cause or encourage the upward flow of oxygen generated by the algae, which allows the oxygen to be released into the atmosphere and cause or encourage the mixing of gas from sparging device 112 within the water and may circulate algae closer to the surface of the pond to promote greater uniformity of light distribution in the algae.

In some embodiments, mixing device 110 or mixing arm 108 may also cause or promote radially outward flow (away from axis 118 and toward perimeter 124) or may cause or promote flow in an angular direction (e.g., in the clockwise direction 119) to help with the removal of harvested algae from pond 102. In such embodiments, mixing tools 142 may be arranged to encourage radially outward flow and/or angular flow of the water. Alternatively, or in addition thereto, sparging nozzles 132 may be arranged to encourage radially outward flow and/or angular flow of the water.

Skimming trough 114 may be configured to harvest or remove portions of algae from pond 102. In FIG. 1, skimming trough 114 extends radially across a portion of pond 102, for example, between pivot connection 106 and pond perimeter 124. In some embodiments, skimming trough may extend beyond perimeter 124, but is not necessary. In some embodiments, skimming trough 114 may be stationary relative to pond 106, but in other embodiments skimming trough 114 may be designed for rotation about pivot axis 118. Skimming trough 114 may be configured to skim water and algae from the top surface of pond 102 to harvest the algae for biofuel production. Skimming trough 114 includes a receiving side 152 to receive water and/or algae and a backside 154 to contain the received water and/or algae. Receiving side 152 may be positioned toward the on-coming direction of pivot arm 108. Some embodiments include a plurality of skimming troughs 114 extending across portions of pond 102 and angularly spaced from each other. In some embodiments, skimming trough 114 may extend across pond 102 along a path that is not radial or does not extend from a central region of the pond 102. As used herein the term "skimming trough" may include any of a device configured to remove algae from water, a trough to receive algae from water, or a combination of these features. The terms "skimming trough" and "skimmer" may be used herein interchangeably, and the terms "algae" and "algae biomass" may be used herein interchangeably.

Water supply device 116 includes a supply line 160 configured to introduce make-up water into pond 102 to replace the water removed via evaporation or skimming trough 114. In some embodiments, supply line 160 may simply pump the make-up water into pond 102 at or near perimeter 124. In other embodiments, however, supply line 160 may be fluidly coupled to a fluid manifold that includes a plurality of supply nozzles 162 spaced apart from each other to distribute the make-up water. Water supply device 116 may also provide other feed material to pond 102, such as nutrients (e.g., bicarbonate), gases, or additional algae strains.

In FIG. 1, water supply device 116 is disposed along the backside 154 of skimming trough 114, having supply nozzles 162 directed in the direction 119, away from skimming trough 114 to encourage fluid motion in the direction 119, with the goal of inducing circulation of algae around pond 102, toward the receiving side 152 of trough 114 for harvesting.

Removal of algae by skimming trough 114 may be augmented by one or more factors such as the tendency of ripe (mature) algae to float to the surface, an upward, an angular, or a radial fluid motion induced by mixing device 110 or mixing arm 108, or a circulation motion caused by injection of water through supply nozzles 162. Any of these several factors may bring algae toward the receiving side 152 of skimming trough 114 to aid with harvesting. In some embodiments, skimming trough 114 may be generally positioned at the surface of pond 102 and at a height that is less than the height H108 of pivot arm 108. In at least one embodiment, the height H108 may be chosen such that pivot arm 108 is below skimming trough 114 and, therefore, travels at a height below the surface of pond 102.

During operation, pivot arm 108 may rotate repeatedly around vertical pivot axis 118 in the angular direction 119, passing skimming trough 114 during each 360 degree cycle. As it rotates, pivot arm 108 moves mixing device 110 (or more specifically, mixing tools 142) and sparging device 112 (or more specifically, sparging nozzles 132) in circular paths to mix and provide sparging to localized portions of pond 102. Each mixing tool 142 and sparging nozzle 132 influences an annular zone of pond 102 as it moves around pond 102.

To avoid interference for embodiments in which arm height H108 is greater than the height of the skimming trough 114, all or a portion of pivot arm 108 may be designed to pivot or otherwise move out of engagement with skimming trough 114. In some embodiments, for example, mixing tools 142 and sparge nozzles 132 may be attached to pivot arm 108 by various pivotable couplings. The pivotable couplings would allow mixing tools 142 and sparge nozzles 132 to pivot and thereby allow pivot arm 108 to bypass skimming trough 114 without skimming trough 114 interfering with angular motion of pivot arm 108. Legs 128 for wheels 126 may also be attached to pivot arm 108 by pivotable couplings for the same reason. Water supply device 116 is also configured to allow pivot arm 108, including its legs 128 and wheels 126, to pass unhindered. For example, in some embodiments, supply line 160 may be plumbed under pond 102 and supply nozzles 162 may extend up from pond bottom 122 at non-interfering locations.

In some embodiments, skimming trough 114 may comprise a segmented or discontinuous structure extending radially outward from the pivot axis 118 toward the outer periphery. More specifically, the skimming trough 114 may include multiple trough segments separated by small spacings or slots to allow the plurality of wheels 126, mixing tools 142, or sparging nozzles 132 of pivot arm 108 to bypass the angular position of skimming trough 114 without pivoting upward and without contact or collision with the skimming trough 114. Each trough segment may collect, feed, and funnel harvested algae downward through a dedicated conduit that extends to a common discharge line located, for example, beneath the pond 102 and fluidically coupled to each dedicated conduit extending from each trough segment. In some embodiments, the spacing between the trough segments may be large enough to accommodate the wheels 126 to pass therethrough, but mixing tools 142 or sparging nozzles 132 are coupled to pivot arm 108 by pivotable couplings giving tools 142 or nozzles 132 the capability to pivot upward and pass over the trough segments.

In some embodiments, system 100 is configured to operate in a pond 102 having a radius in the range of 245 to 370 meters (approximately 805 to 1,215 feet) and a depth in the range of 0.20 to 0.40 m (approximately 0.67 to 1.30 ft). In these embodiments, the size ratio for the pond (i.e., radius-to-depth ratio) may be in the range of 610 to 1900. Other embodiments may use a pond having a size the is greater than or less than the stated range of radius or the stated range of depth. Similarly, pivot arm 108 may have a radius in the range of 245 to 370 meters, but other embodiments may include a pivot arm 108 having a radius outside the stated range. As will be appreciated, however, such dimensions for pond 102 are provided merely for illustrative purposes and, therefore, should not be considered limiting to the scope of the present disclosure.

In various embodiments, pivot arm 108 and its fluid mixing device 110, wheels 126, or sparging device 112 may be configured to travel under skimming trough 114. For example, the pivot arm 108, the fluid mixing device 110, the wheels 126, the sparging device 112 and the various associated components may be configured to be submerged in the pond 102. Although the fluid mixing device 110 and the sparging device 112 of FIG. 1 and FIG. 2 are shown to extend below pivot arm 108 in various figures presented herein, some embodiments may include fluid mixing device 110 with mixing tools 142 or sparging device 112 with nozzles 132 that extend above pivot arm 108, without departing from the scope of the disclosure.

Figure 3:
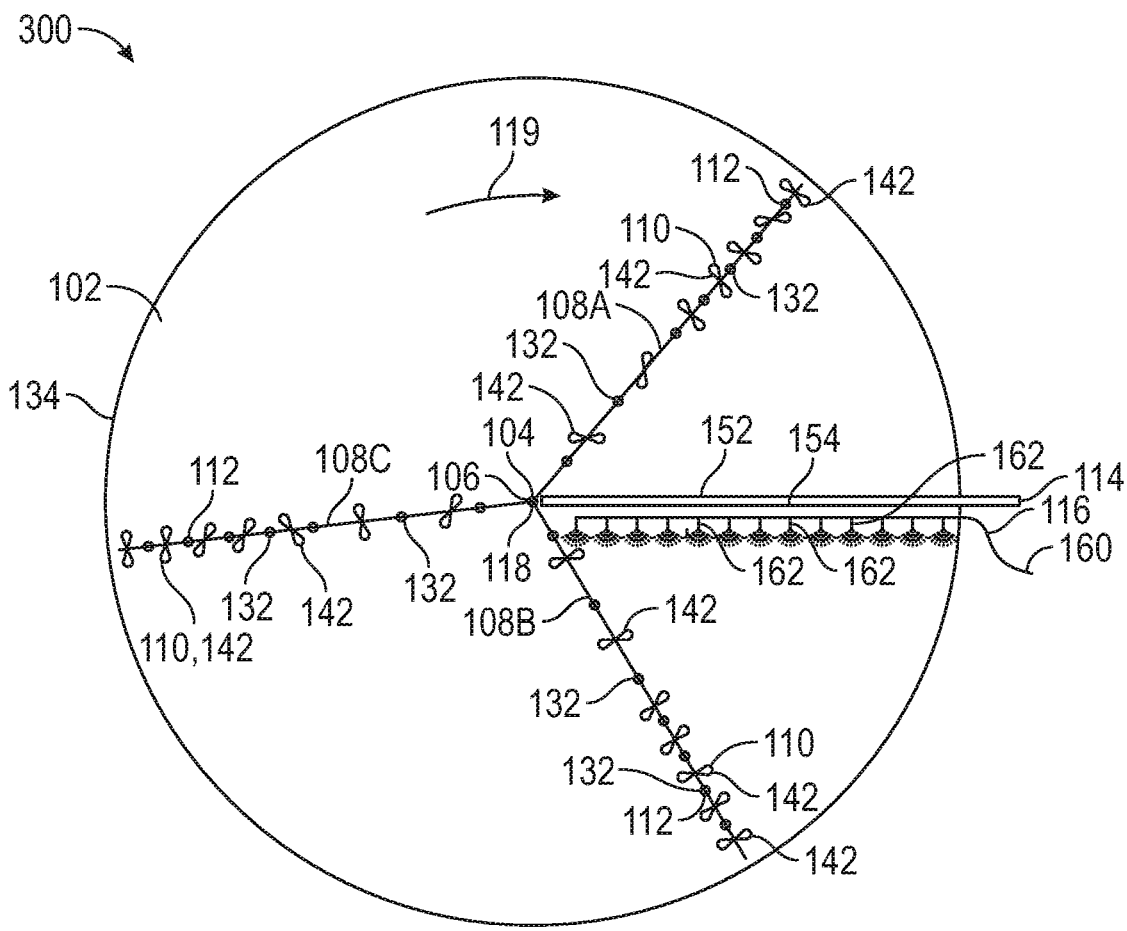
FIG. 3 is a top-view diagram of another example system for growing algae in a pond, according to various embodiments of the present disclosure.

FIG. 3 is a schematic top view of another example system 300 for growing algae, according to one or more additional embodiments. System 300 is similar in some respects to system 100 of FIG. 1 and FIG. 2, and therefore system 300 may be best understood with reference thereto, where like numerals will represent like components that may not be described again in detail. In general, unless specifically described as being different, the configurations and the operations, including the potential variations, described for system 100, are applicable to system 300. Similar to system 100, for instance, system 300 includes pivot connection 106 defining vertical pivot axis 118, skimming trough 114, and water supply device 116.

Unlike system 100 of FIGS. 1-2, however, system 300 may include a plurality of pivot arms 108 for mixing fluid in pond 102. More specifically, system 300 includes a set of three horizontally extending pivot arms 108, depicted as pivot arms 108A, 108B, 108C. Pivot arms 108A, B, C may be angularly spaced from each other and are coupled to pivot connection 106 to travel along an arcuate or circular sweeping path about pivot axis 118. Each pivot arm 108A, B, C is coupled to corresponding mixing devices 110 and sparging devices 112, which are to be disposed in pond 102 to move through the water as the corresponding pivot arm 108A, B, C moves about pivot axis 118. In some embodiments, the sparging devices 112 on each pivot arm 108A, B, C may share a common supply line (e.g., supply line 130 of FIG. 2).

Accompanied by corresponding mixing devices 110 and sparging devices 112, pivot arms 108A, B, C may rotate simultaneously about pivot axis 118, maintaining a fixed or variable angular spacing. In some embodiments, any of the pivot arms 108A, B, C may have its own pivot connection 106, which may be mounted at different heights along axis 118, instead of sharing a common pivot connection. Although shown with three pivot arms 108A, B, C, embodiments are contemplated herein that include two, four, or another suitable number of pivot arms coupled at a common pivotal coupling.

In some embodiments that include multiple pivot arms, a first pivot arm 108 includes a mixing device 110 and lacks a sparging device, and a second pivot arm 108 includes a sparging device 112 and lacks a mixing device.

Figure 4:
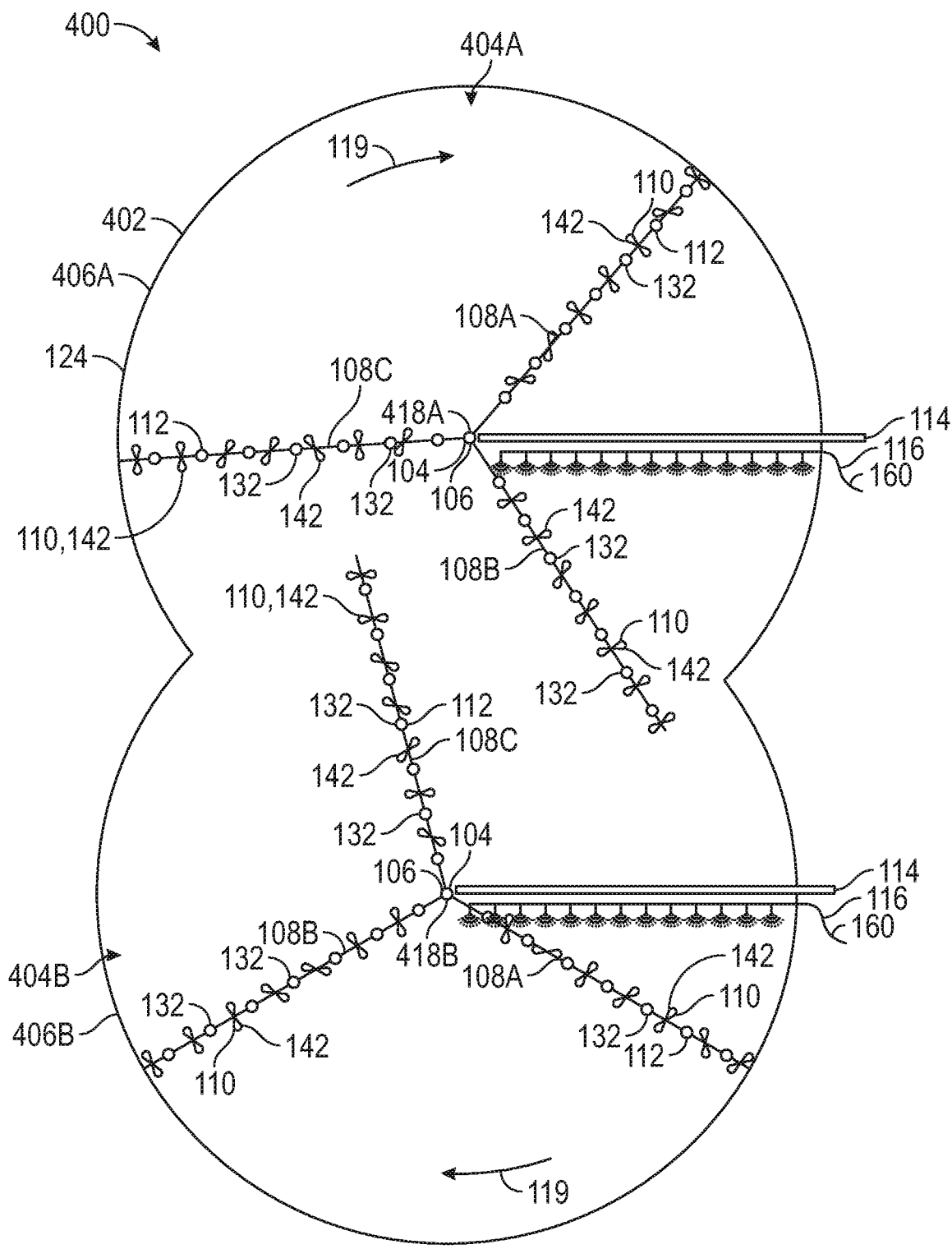
FIG. 4 is a top-view diagram of another example system for growing algae incorporated with a pond, according to various embodiments of the present disclosure.

FIG. 4 is a schematic top view of another example system 400 for growing algae, according to one or more additional embodiments. System 400 is similar in some respects to system 100 of FIG. 1 and FIG. 2 and system 300 of FIG. 3, and therefore system 400 may be best understood with reference thereto, where like numerals will represent like components that may not be described again in detail. In general, unless specifically described as being different, the configurations and the operations, including the potential variations, described for systems 100 and 300, are applicable to system 400.

As illustrated, system 400 includes a plurality of sets 404A, 404B of pivot arms 108 for mixing fluid in a pond 402, which includes two overlapping circular regions 406A, 406B defined by pond perimeter 124. The first set 404A of pivot arms 108 is arranged in the first circular region 406A of the pond 402, and the second set 404B of pivot arms 108 is arranged in the second circular region 406B of the pond 402. Some other embodiments like system 400 may include three, four, or another suitable number of sets of pivot arms. Some other examples may include a pond with three, four, or another suitable number of overlapping regions. The overlapping regions may be circular.

Each set 404A, 404B of pivot arms is similar to the set of pivot arms of system 300 (FIG. 3). More specifically, each set includes three pivot arms 108A, 108B, 108C coupled at a corresponding pivot connection 106 and angularly spaced from each other. The first set 404A and its corresponding pivot connection 106 are disposed at pivot axis 418A, which is at the center of pond region 406A. The pivot arms 108A, 108B, 108C of the first set 404A are configured to travel along an arcuate or circular sweeping path about the pivot axis 418A. The second set 404B and its corresponding pivot connection 106 are likewise disposed at a pivot axis 418B at the center of pond region 406B. The pivot arms of the second set 404B are configured to travel along an arcuate or circular sweeping path about pivot axis 418B. The sweeping path of the pivot arms of the second set 404B overlaps of the sweeping path of the pivot arms of the first set 404A.

Each pivot arm 108A, B, C of each set 404A, 404B is coupled to a mixing device 110 and a sparging device 112, which are to be disposed in pond 102 to move through the water as the corresponding pivot arm 108A, B, C moves about the associated pivot axis 418A, B. The timing of the rotation of the pivot arms 108A, B, C of each set 404A, 404B is designed or operated so as not to interfere (e.g., collide) with the pivot arms of the other set 404A, 404B, and, of course, so as not to interfere with pivot arms of the same set 404A, 404B. In this example, system 400 also includes two skimming troughs 114 and two water supply devices 116, one of each associated with each set 404A, 404B of pivot arms 108.

Figure 5:
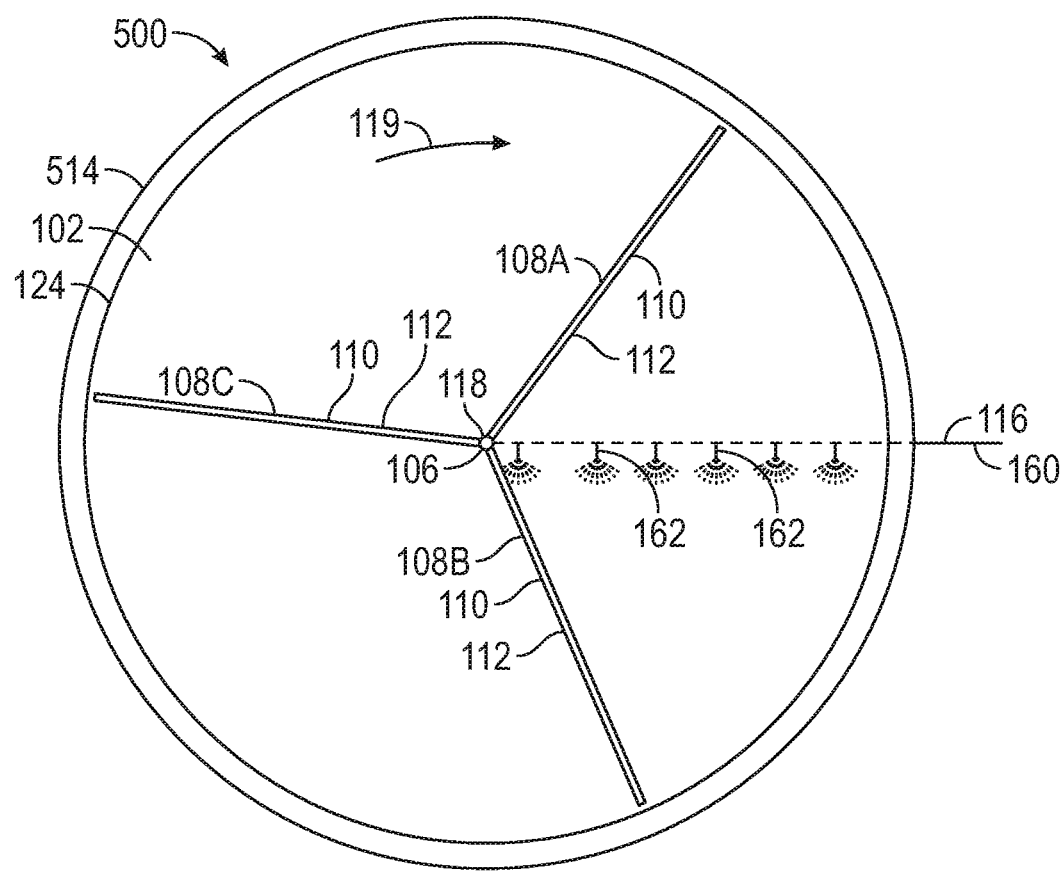
FIG. 5 is a top-view diagram of another example system for growing algae in a pond, according to various embodiments of the present disclosure.

FIG. 5 is a schematic top view of another example system 500 for growing algae, according to one or more additional embodiments. System 500 is similar in some respects to system 100 of FIG. 1 and FIG. 2 and system 300 of FIG. 3, and therefore system 500 may be best understood with reference thereto, where like numerals will represent like components that may not be described again in detail. In general, unless specifically described as being different, the configurations and the operations, including the potential variations, described for systems 100 and 300, are applicable to system 500.

As illustrated, system 500 includes water supply device 116 and a set of three horizontally extending pivot arms 108A, 108B, 108C coupled to pivot connection 106 or multiple pivot connections 106 at pivot axis 118. Although shown with three pivot arms 108A, B, C, some other embodiments like system 500 include two, four, or another suitable number of pivot arms coupled at a common pivotal coupling. Pivot arms 108A, B, C may be angularly spaced from each other and, as previously described, each pivot arm 108A, B, C may be accompanied by mixing device 110 and sparging device 112. In FIG. 5, a single block on the diagram corresponds to a set that includes a pivot arm (e.g., an arm 108A, B, C), a mixing device 110, and a sparging device 112.

Each pivot arm 108A, B, C may be mounted on a plurality of motor-driven wheels, such as wheels 126 of FIG. 2. Water supply device 116 is shown with a supply line 160 extending under pond 102 and a plurality of supply nozzles 162 extending upward from the bottom of pond 102 to distribute make-up or recycled water or other feed material. The spacing of supply nozzles 162 is selected so as not to interfere with the mixing devices 110, the sparging devices 112, and the wheels on the several pivot arms 108A, B, C.

Unlike systems 100 and 300 of FIGS. 1-3, system 500 includes a circumferentially extending (annular) skimming trough 514 disposed about at least a portion of pond perimeter 124 and may include a below-grade trench. With the inclusion of the perimeter-mounted skimming trough 514 and with water supply device 116 configured as described, pivot arms 108A, B, C in system 500 may be built without pivotable couplings for mixing tools 142 (FIG. 2) of mixing device 110, for sparge nozzles 132 (FIG. 2) of sparging device 112, and legs 128 (FIG. 2) for wheels 126 (FIG. 2). These components may remain at a fixed orientation with respect to the body of the corresponding pivot arm 108A, B, C. For example, mixing tools 142, sparge nozzles 132, and legs 128 may extend downward from pivot arm 108A, B, C without concern about interference with a skimming through while pivot arms 108A, B, C rotate about pond 102. Rotation about pond 102 by pivot arms 108A, B, C and the components attached to the pivot arms may generate an outward movement of fluid and algae, at least at the upper surface of pond 102, causing some of the algae to be captured in skimming trough 514.

In various embodiment, a skimming trough 514 disposed around the perimeter of a pond replaces or supplements skimming troughs 114 shown in FIGS. 1, 3, and 4, that extend radially outward from a central location in a pond. Skimming trough 514 arranged about the perimeter of pond 102 may also be implemented in systems that include a single pivot arm 108, such as system 100 of FIG. 1. Skimming trough 514 may also be implemented in configurations that include multiple sets of concentrically mounted pivot arms, such sets 404A, 404B of pivot arms shown in FIG. 4, which may be installed in a pond having multiple, overlapping circular regions.

Figure 6:
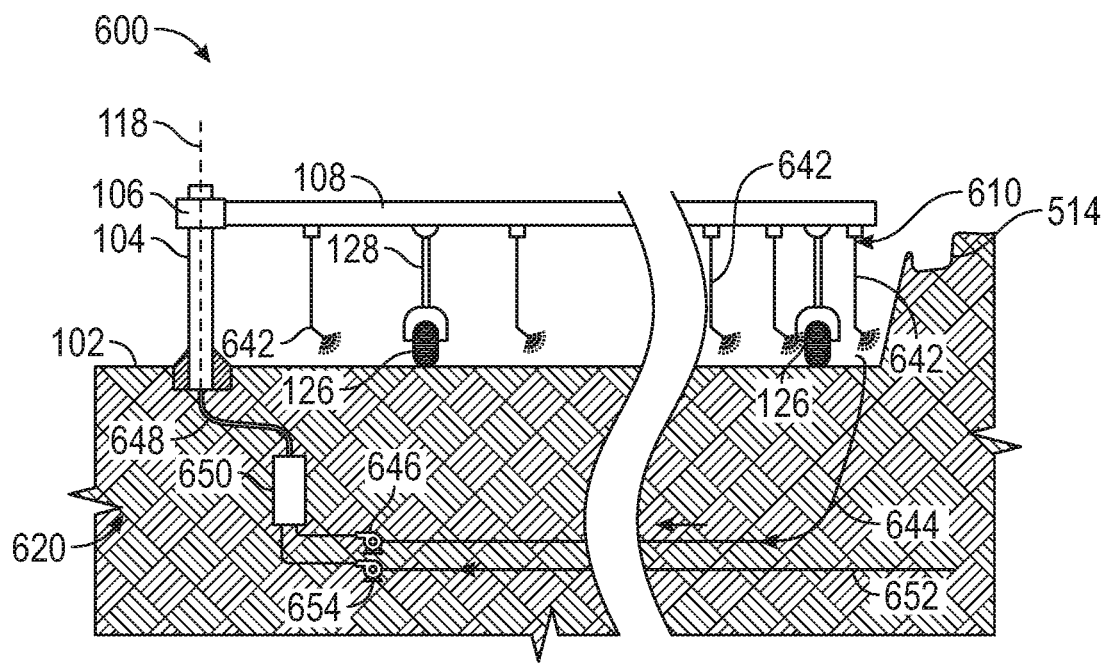
FIG. 6 illustrates a side view of a system for growing algae in a pond, according to various embodiments of the present disclosure.

FIG. 6 is a side view of a system for growing algae in a pond, including a pivot arm mounted to a pivot connection and integrated with a fluid nozzle-type mixing device. System 600 is similar in some respects to systems described with respect to FIGS. 1-5, and therefore system 600 may be best understood with reference thereto, where like numerals will represent like components that may not be described again in detail. In general, unless specifically described as being different, the configurations and the operations, including the potential variations, described for systems 100, 300, 400, and 500 are applicable to system 600.

As illustrated, system 600 is shown installed in and incorporated with pond 102 having a circumferentially extending skimming trough 514 formed to include a below-grade trench disposed around at least a portion of the pond's perimeter. System 100 also includes a horizontally extending pivot arm 108 coupled to pivot connection 106, which includes stationary base or post 104 and allows pivot arm 108 to rotate about pivot axis 118. In some embodiments, pivot arm 108 may be supported by wheels 126 arranged at the end of legs 128. System 100 may also include a water supply device 116 (FIGS. 1, 5).

System 600 further includes a fluid nozzle-type mixing device 610 coupled to pivot arm 108 and integrated with a fluid supply system 620. Mixing device 610 travels with pivot arm 108 as it moves about pivot axis 118. Mixing device 610 comprises a plurality of mixing tools, including one or more fluid nozzles 642 spaced apart from each other along pivot arm 108 and extending into pond 102.

Fluid supply system 620 includes a fluid recirculation line 644 and a recirculation pump 646 fluidically coupled to fluid nozzles 642 by a fluid supply line 648. Fluid supply system 620 may also include a mixing chamber 650 and a sparging supply line 652, which may include a sparging pump or compressor 654. Supply line 648 extends through base or post 104, through pivot connection 106, and into pivoting arm 108. Pivot connection 106 includes a rotatable coupling incorporated into supply line 648 to accommodate the rotation of a downstream portion supply line 648 disposed in pivot arm 108 relative to an upstream portion of supply line 648 disposed in post 104 without leaking fluid.

In operation, fluid supply system 620 is configured to recirculate pond water from pond 102, which may be drawn into recirculation line 644 by recirculation pump 646. Recirculation line 644 may be positioned to extract fluid from any suitable location within pond 102. Fluid supply system 620 and its sparging supply line 652 are configured to provide a stream of one or more gases, such as carbon dioxide, flue gas, air, or another gas containing carbon dioxide to be injected into pond 102. Mixing chamber 650 is fluidically coupled to fluid recirculation line 644 and is fluidically coupled to sparging supply line 652. During operation, mixing chamber 650 may receive pond water and gases from fluid recirculation line 644 and sparging supply line 652, respectively, and may receive other nutrients. Mixing chamber 650 mixes and discharges a corresponding mixture of fluids to supply line 648 to be discharged through mixing nozzles 642, which are fluidically coupled to fluid supply system 620.

In some embodiments, one or more of fluid nozzles 642 may direct their discharge downward and radially outward relative to pivot axis 118. In other embodiments, fluid nozzles 642 may direct fluid discharge in any suitable direction in pond 102, including upward, radially inward, and tangentially relative to axis 118. In yet other embodiments, fluid nozzles 642 may direct fluid discharge in two or more of the foregoing directions.

Some embodiments of system 600 can include a sparging device 112 (FIGS. 1-2) with a sparging supply line 130 (FIG. 2) separate from fluid nozzle-type mixing device 610 and fluid supply system 620. Although shown with a circumferentially extending skimming trough 514, some embodiments of system 600 include a skimming trough 114 that extends across a portion of a pond, and fluid nozzle-type mixing device 610 and wheels 126 may be attached to pivot arm 108 by pivotable couplings, configuring them to move over the skimming trough. In some embodiments, a fluid nozzle-type mixing device may include a water supply device configured to provide the benefits of a water supply device 116, for example.

Listing of Exemplary Embodiments

The present disclosure provides, among others, the following embodiments, each of which may be considered as optionally including any alternate embodiments.

Clause 1. A system for growing algae that includes a pivot arm pivotally coupled to a pivot connection positioned in a pond containing water and algae, and a mixing device coupled to the pivot arm and extending into the pond to mix the water and the algae as the pivot arm rotates.

Clause 2. The system of Clause 1, wherein the mixing device comprises one or more mixing tools coupled to the pivot arm and extending into the pond.

Clause 3. The system of Clause 2, wherein the one or mixing tools are selected from the group consisting of a propeller, a screw profile, a fluid nozzle, a jet, a sparging nozzle, a wave generator, and any combination thereof.

Clause 4. The system of any of the Clauses 2 or 3, wherein the one or more mixing tools comprise a plurality of mixing tools spaced apart from each other along the pivot arm at intervals that decrease in a radial direction away from the pivot connection.

Clause 5. The system of any of the Clauses 1 to 4, wherein the pivot arm is a first pivot arm and the mixing device is a first mixing device, the system further comprises: a second pivot arm pivotally coupled to the pivot connection and angularly spaced from the first pivot arm; and a second mixing device coupled to the second pivot arm and including one or more mixing tools coupled to the second pivot arm and extending into the pond.

Clause 6. The system of any of the Clauses 1 to 5, wherein the pond has a bottom and the pivot arm is supported by one or more wheels engageable with the bottom.

Clause 7. The system of any of the Clauses 1 to 6, further comprising a skimming trough extending radially outward from a center of the pond to remove algae from the pond.

Clause 8. The system of any of the Clauses 1 to 7, further comprising a skimming trough positioned at a perimeter of the pond to remove algae from the pond.

Clause 9. The system of any of the Clauses 1 to 8, wherein the pivot connection is a first pivot connection, the pivot arm is a first pivot arm, and the mixing device is a first mixing device, the system further comprising: a second pivot arm pivotally coupled to a second pivot connection positioned in the pond; and a second mixing device coupled to the second pivot arm and extending into the pond to mix the water and the algae as the second pivot arm rotates, wherein the first pivot arm travels along a first sweeping path and the second pivot arm travels along a second sweeping path that overlaps the first sweeping path.

Clause 10. The system of any of the Clauses 1 to 9, wherein first pivot connection is disposed at a center of a first circular region defined by the pond and the second pivot connection is disposed at a center of a second circular region defined by the pond, and wherein the first and second circular regions overlap.

Clause 11. The system of any of the Clauses 1 to 10, further comprising a sparging device including at least one sparging nozzle coupled to the pivot arm and extending into the pond to deliver one or more gases to the water and the algae.

Clause 12. The system of any of the Clauses 1 to 11, wherein the mixing device comprises one or more fluid nozzles extending into the pond and fluidically coupled with a fluid supply system, and wherein the fluid supply system comprises a fluid recirculation line extending into the pond to receive a portion of the water.

Clause 13. The system of any of the Clauses 12, wherein the fluid supply system further comprises a sparging supply line to deliver a gas and a mixing chamber to mix the gas with the water from the fluid recirculation line.

Clause 14. A method for growing algae that includes introducing algae and water into a pond having a pivot arm pivotally coupled to a pivot connection positioned in the pond, rotating the pivot arm about a pivot axis extending through the pivot connection, and mixing the water and the algae with a mixing device coupled to the pivot arm as the pivot arm rotates.

Clause 15. The method of any of Clause 14, wherein the pivot arm is a first pivot arm, and the mixing device is a first mixing device, the method further comprising: rotating a second pivot arm about the pivot axis and angularly spaced from the first pivot arm; and mixing the water and the algae with a second mixing device coupled to the second pivot arm as the second pivot arm rotates.

Clause 16. The method of any of Clause 14 or 15, further comprising removing algae from the pond with a skimming trough extending across a portion of the pond.

Clause 17. The method of any of the Clauses 14 to 16, further comprising removing algae from the pond with a skimming trough positioned at a perimeter of the pond.

Clause 18. The method of any of the Clauses 14 to 17, wherein mixing the water and the algae with the mixing device comprises inducing upward fluid motion and radially outward fluid motion in the pond with the mixing device.

Clause 19. The method of any of the Clauses 14 to 18, wherein the pivot connection is a first pivot connection arranged in a first circular region of the pond, the pivot arm is a first pivot arm, and the mixing device is a first mixing device, the method further comprising: rotating a second pivot arm about a pivot axis of a second pivot connection arranged in a second circular region of the pond, wherein the first and second circular regions partially overlap; and mixing the water and the algae in the second circular region of the pond with a second mixing device coupled to the second pivot arm.

Clause 20. The method of any of Clause 19, further comprising: traversing a first sweeping path with the first pivot arm; and traversing a second sweeping path that overlaps the first sweeping path with the second pivot arm.

In various embodiments according to the present disclosure, a skimming trough or skimmer is configured to remove algae into an above-grade trough or a below-grade trough using bridge or tunnel mechanisms. In some embodiments, a skimmer may be located or configured to remove algae from the bottom of a pond into a below-grade trench, which may be advantageous if the algae species were to settle in the water/slurry.

Nomenclature

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms used herein, including the claims, have their plain, ordinary meaning unless otherwise explicitly and clearly defined by the patentee. Moreover, the indefinite articles "a" or "an," as used herein, including the claims, are defined herein to mean one or more than one of the element that it introduces.

The term "or" as used in a phrase such as "A or B" herein is intended to include optionally of any of the following: "A" alone, "B" alone, and, where feasible, "A and B." Ordinal numbers such as first, second, third, etc. do not indicate a quantity but are used for naming and reference purposes. In addition, ordinal numbers used in the claims in reference to a component or feature may differ from the ordinal numbers used in the written description for the corresponding component or feature. For example, a "second object" in a claim might be described as a "third object" or may be described without an ordinal number in the written description.

As used herein, including the claims, the term "line" for fluid communication may include any of the following pipe, piping, tubing, hose, fittings, valves, gauges, check valves, flow meters, filters, and the like.

Unless otherwise indicated, all numbers expressing quantities of ingredients, properties such as length, volume, mass, molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

For the sake of clarity, not all features of a physical embodiment are described or shown in this application. It is understood that in the development of a physical embodiment incorporating the embodiments of the present disclosure, numerous implementation-specific decisions must be made to achieve the developer's goals, such as compliance with system-related, business-related, government-related, and other constraints, which vary by implementation and from time to time. While a developer's efforts might be time-consuming, such efforts would be, nevertheless, a routine undertaking for those of ordinary skill in the art and having benefit of this disclosure.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The illustrative embodiments disclosed herein suitably may be implemented in the absence of any element that is not specifically disclosed herein and/or any optional element disclosed herein. While components, compositions, and methods are described in terms of "comprising," "containing," or "including" various components or steps, the components, compositions, and methods can also "consist essentially of" or "consist of" the various components and steps. For the methods herein, the order of various process steps may be rearranged in some embodiments and yet remain within the scope of the disclosure, including the claims.

The invention claimed is:

1. A system for growing algae, comprising:
    a pivot arm pivotally coupled to a pivot connection positioned in a pond containing water and algae; and
    a mixing device coupled to the pivot arm and extending into the pond to mix the water and the algae as the pivot arm rotates; and
    a skimming trough detached from the pivot arm and positioned at a top surface of the pond to remove portions of the algae from the top surface of the pond, wherein the skimming trough is stationary relative to the pond.

2. The system of claim 1, wherein the mixing device comprises one or more mixing tools coupled to the pivot arm and extending into the pond.

3. The system of claim 2, wherein the one or more mixing tools are selected from the group consisting of a propeller, a screw profile, a fluid nozzle, a jet, a sparging nozzle, a wave generator, and any combination thereof.

4. The system of claim 2, wherein the one or more mixing tools comprise a plurality of mixing tools spaced apart from each other along the pivot arm at intervals that decrease in a radial direction away from the pivot connection.

5. The system of claim 1, wherein the pivot arm is a first pivot arm and the mixing device is a first mixing device, the system further comprises:
    a second pivot arm pivotally coupled to the pivot connection and angularly spaced from the first pivot arm; and
    a second mixing device coupled to the second pivot arm and including one or more mixing tools coupled to the second pivot arm and extending into the pond.

6. The system of claim 1, wherein the pond has a bottom and the pivot arm is supported by one or more wheels engageable with the bottom.

7. The system of claim 1, wherein the skimming trough extends radially outward from a center of the pond to remove the portions of the algae from the pond.

8. The system of claim 1, wherein the skimming trough is positioned at a perimeter of the pond to remove the portions of the algae from the pond.

9. The system of claim 1, wherein the pivot connection is a first pivot connection, the pivot arm is a first pivot arm, and the mixing device is a first mixing device, the system further comprising:
    a second pivot arm pivotally coupled to a second pivot connection positioned in the pond; and
    a second mixing device coupled to the second pivot arm and extending into the pond to mix the water and the algae as the second pivot arm rotates, wherein the first pivot arm travels along a first sweeping path and the second pivot arm travels along a second sweeping path that overlaps the first sweeping path.

10. The system of claim 9, wherein first pivot connection is disposed at a center of a first circular region defined by the pond and the second pivot connection is disposed at a center of a second circular region defined by the pond, and wherein the first and second circular regions overlap.

11. The system of claim 1, further comprising a sparging device including at least one sparging nozzle coupled to the pivot arm and extending into the pond to deliver one or more gases to the water and the algae.

12. The system of claim 1, wherein the mixing device comprises one or more fluid nozzles extending into the pond and fluidically coupled with a fluid supply system, and wherein the fluid supply system comprises a fluid recirculation line extending into the pond to receive a portion of the water.

13. The system of claim 12, wherein the fluid supply system further comprises a sparging supply line to deliver a gas and a mixing chamber to mix the gas with the water from the fluid recirculation line.

14. A method for growing algae, comprising:
introducing algae and water into a pond having a pivot arm pivotally coupled to a pivot connection positioned in the pond;
rotating the pivot arm about a pivot axis extending through the pivot connection;
mixing the water and the algae with a mixing device coupled to the pivot arm as the pivot arm rotates; and
removing portions of the algae from a top surface of the pond with a skimming trough detached from the pivot arm and positioned at the top surface of the pond, wherein the skimming trough is stationary relative to the pond.

15. The method of claim 14, wherein the pivot arm is a first pivot arm, and the mixing device is a first mixing device, the method further comprising:
rotating a second pivot arm about the pivot axis and angularly spaced from the first pivot arm; and
mixing the water and the algae with a second mixing device coupled to the second pivot arm as the second pivot arm rotates.

16. The method of claim 14, wherein the skimming trough extends across a portion of the pond.

17. The method of claim 14, wherein the skimming trough is positioned at a perimeter of the pond.

18. The method of claim 14, wherein mixing the water and the algae with the mixing device comprises inducing upward fluid motion and radially outward fluid motion in the pond with the mixing device.

19. The method of claim 14, wherein the pivot connection is a first pivot connection arranged in a first circular region of the pond, the pivot arm is a first pivot arm, and the mixing device is a first mixing device, the method further comprising:
rotating a second pivot arm about a pivot axis of a second pivot connection arranged in a second circular region of the pond, wherein the first and second circular regions partially overlap; and
mixing the water and the algae in the second circular region of the pond with a second mixing device coupled to the second pivot arm.

20. The method of claim 19, further comprising:
traversing a first sweeping path with the first pivot arm; and
traversing a second sweeping path that overlaps the first sweeping path with the second pivot arm.

* * * * *